United States Patent [19]
Jones

[11] Patent Number: 5,591,642
[45] Date of Patent: Jan. 7, 1997

[54] FLUID DISPENSING METHOD

[75] Inventor: Donald Jones, Sacramento, Calif.

[73] Assignee: Dade MicroScan Inc., West Sacramento, Calif.

[21] Appl. No.: 460,358

[22] Filed: Jun. 2, 1995

Related U.S. Application Data

[62] Division of Ser. No. 438,459, May 10, 1995, which is a continuation of Ser. No. 89,878, Jul. 9, 1993, abandoned.

[51] Int. Cl.$^6$ .......................... G01N 35/02; G01N 35/10
[52] U.S. Cl. .................. 436/43; 436/47; 422/65
[58] Field of Search ................ 436/43, 47, 52; 422/62, 65, 67, 100, 109

[56] References Cited

U.S. PATENT DOCUMENTS

| | | | |
|---|---|---|---|
| 4,496,958 | 1/1985 | Brandt et al. | |
| 4,952,518 | 8/1990 | Johnson et al. | 422/65 |
| 5,055,263 | 10/1991 | Meltzer | 422/65 |
| 5,122,342 | 6/1992 | McCulloch et al. | 422/67 |

FOREIGN PATENT DOCUMENTS

| | | |
|---|---|---|
| 2113408 | 8/1983 | United Kingdom . |
| 2143800 | 2/1985 | United Kingdom . |
| 2148151 | 5/1985 | United Kingdom . |
| WO93/09441 | 5/1993 | WIPO . |

OTHER PUBLICATIONS

*Robotics: Choice and Implementation*; 8386 Chemometrics and Intelligent Laboratory Systems; 17 (1992) Oct., No. 1, Amsterdam, NE; Elsevier Science Publishers B.V. 1992.

*Primary Examiner*—Lyle A. Alexander
*Attorney, Agent, or Firm*—Terry L. Miller

[57] ABSTRACT

A chemical analyzer (10) includes a fluid dispensing system (46) with a carrier member (18) and fluid dispensing head (72). The carrier member (18) includes a docking fixture (52) and the fluid dispensing head includes a docking receptacle (54). By engagement of the docking fixture and receptacle the carrier member carries the fluid dispensing head to a position above a recess (34) into which fluid is precisely dispensed. The carrier member also returns the fluid dispensing head to a storage location (64) substantially separating the fluids to be dispensed from the environment of the analyzer. When the fluid dispensing head is in its storage location the carrier member may disengage to perform other functions in the analyzer.

4 Claims, 4 Drawing Sheets

FLUID DISPENSING METHOD

This is a division of application Ser. No. 08/438,459 filed on May 10, 1995; which is a continuation of 08/089,878 filed on Jul. 9, 1993 now abandoned.

BACKGROUND OF THE INVENTION

1. Field of the Invention

The present invention is in the field of fluid dispensing apparatus and methods. More particularly, the present invention relates to fluid dispensing apparatus and methods for analytical systems used in a variety of environments to carry out analytical, laboratory, and clinical procedures. These analytical systems are generally automatic or semiautomatic and are used in hospital and clinical environments. Generally such analytical systems are used to process patient specimens including, for example, tissue and bodily fluid samples, for detecting the presence of various chemical compounds and organisms therein.

2. Discussion of the Related Technology

Conventional chemical analyzers and incubators have been known which employ fluid dispensing apparatus. For example, microbiological analytical systems are known currently which carry out automated antimicrobic susceptibility testing procedures using both photometric and fluorometric detection methods. U.S. Pat. Nos. 4,643,879; 4,676,951; and 4,681,741, describe certain features of such a system.

Generally, the conventional analyzer includes a vertically extending annular incubation chamber within which is loaded a plurality of specimen trays each defining plural recesses within which a portion of selected specimen material is placed for processing. On the specimen trays the recesses are arranged in rows and columns to form a rectangular grid. The specimen trays in a horizontal disposition and each with an individual cover are stacked vertically one above the other and are vertically spaced apart in plural tray racks within the incubation chamber.

The incubation chamber includes a carousel moving the specimen trays in their racks around the annulus of the incubation chamber. A column structure extends vertically up the center of the incubation chamber annulus, and a carrier is vertically movable on this column. The tray racks are moved about the incubation chamber to bring a selected rack in front of the carrier. This carrier includes an extensible shelf which may be extended into the tray storage rack to lift a particular specimen tray therefrom. The rack itself is configured so that the tray cover stays in the rack. Consequently, the carrier shelf receives the tray without its cover so that the recesses within which the specimens are carried are open while the tray is on the carrier shelf. The specimen trays are formed of translucent or transparent material, and the carrier shelf is open below each recess.

On the carrier a first work station includes an elongate bar-like photometric analyzer aligning with the rows of specimen recesses. In order to photometrically analyze the contents of the recesses in a particular row of the recesses the shelf is extended or retracted to align the particular specimen recess row with the photometric analyzer. The photometric sensor has a plurality of separate sensor heads each of which aligns with one of the recesses in the particular row, and light transmission through the specimen material is used to detect certain changes, such as turbidity.

The carrier also includes a shuttle member moving from side to side over the specimen tray and carrying a fluorometric analyzer. The fluorometric analyzer has a single sensor head and is brought into alignment with a particular specimen recess by extension or retraction of the shelf, in conjunction with side to side movement of the shuttle. Similarly, the shuttle carries a fluid dispensing head from which various liquid reagents may be dispensed into particular ones of the specimen recesses. This fluid dispensing head includes a separate fluid dispensing nozzle for each of the reagents. These nozzles are arranged in a rectangular grid so that the coordinates of each nozzle opening relative to the shuttle member are known. By extension and retraction of the tray and side to side movement of the shuttle member, a particular nozzle opening of the fluid dispensing head may be brought into vertical congruence with a particular recess of the specimen tray for dispensing of reagent liquid into the recess.

However, experience has shown that having the fluid dispensing head permanently carried on the shuttle member results in some disadvantages. First of all, the movements of the carrier and shuttle in the incubation chamber require that the liquid reagent sources be connected to the fluid dispensing head with conduits of considerable length. The length of these conduits becomes a disadvantage When one considers the small volume of the reagents which must be dispensed into the specimen recess, along with the precision with which these reagents must be measured out.

Additionally, some of the reagents themselves are acidic, caustic or otherwise corrosive. Consequently, taking the reagent dispensing head into the incubation volume exposes many parts of the incubator to the possibility of deterioration from the corrosive natures of the reagent liquids. Also, the incubator itself involves an environment of elevated temperature which may result in evaporation of volatile constituents of some of the reagents.

Still additionally, the reagents which do experience evaporation of some constituent thereof may undergo an increase in their viscosity so that they do not dispense accurately. In extreme cases, the reagent may evaporate to the point of leaving a crust of solids which blocks the individual dispensing nozzle for that reagent. Even in those cases where the reagent crust does not block the dispensing nozzle, the presence of the crust can result in dispensed reagent going astray instead of into the intended specimen recess. All of these difficulties represent possible operating interruptions for a clinical analyzer, with attendant possible loss of test results for the specimens in process, and delay of processing of other specimens awaiting analysis. In every case, evaporation and crusting of reagent represents loss of reagent which is not used in processing specimens.

SUMMARY OF THE INVENTION

In view of the above, an object for this invention is to provide a fluid dispensing apparatus and method for use with a specimen analyzer of the above-described character which does not dispense the reagent fluids in the incubation part of the analyzer.

More particularly, an object for the present invention is to provide a fluid dispensing apparatus in which the fluid dispensing head is separable from the carrier and shuttle thereon, and is engageable therewith for fluid dispensing.

Still more particularly, the present invention has as an object the provision of a fluid dispensing apparatus of the above-described character in which the fluid dispensing nozzle is disposed in a fluid dispensing work station, and the carrier and shuttle move to this work station where the latter joins with the nozzle for fluid dispensing.

Yet an additional object is to provide in the above-described fluid dispensing apparatus, a cooperative docking structure, part of which is carried on the shuttle, and the mating part of which forms part of the fluid dispensing nozzle, so that a precise and repeatable positioning of the fluid dispensing nozzles relative to the carrier and shuttle is achieved.

Accordingly, the present invention provides a fluid dispensing apparatus including a fluid dispensing head having plural fluid dispensing nozzles, a carrier translatable along a first axis and including a shuttle member translatable along a second axis perpendicular to said first axis, and said shuttle and fluid dispensing head defining cooperating means for selectively engaging and disengaging said fluid dispensing head with said shuttle in response to first, second, and third movements of said carrier and shuttle along said first, second, and first axis, respectively, for moving said fluid dispensing head when engaged with said shuttle for dispensing fluid to a first receptacle therefor, and when disengaged for disposing said fluid dispensing head upon a second receptacle for receiving fluid therefrom.

An advantage of the present invention resides in the separation of the fluid dispensing head from the carrier and shuttle. Consequently, the fluid dispensing head need never travel into the incubation chamber of an analyzer with all of the attendant disadvantages such disposition of the dispensing head entails.

Additionally, the fluid dispensing head is positively positioned reliably and repeatably relatively to the carrier and shuttle of an analyzer so that dispensing of reagent fluids to a particular recess of a specimen tray can be assured.

These and other additional objects and advantages of the present invention will appear from a reading of the following description of a particularly preferred exemplary embodiment of the invention taken in conjunction with the appended drawing Figures.

DESCRIPTION OF THE DRAWING FIGURES

FIG. 1 provides a fragmentary perspective view of an analyzer including fluid dispensing apparatus according to the present invention, with parts thereof broken away or omitted for clarity of illustration;

Figure 2:
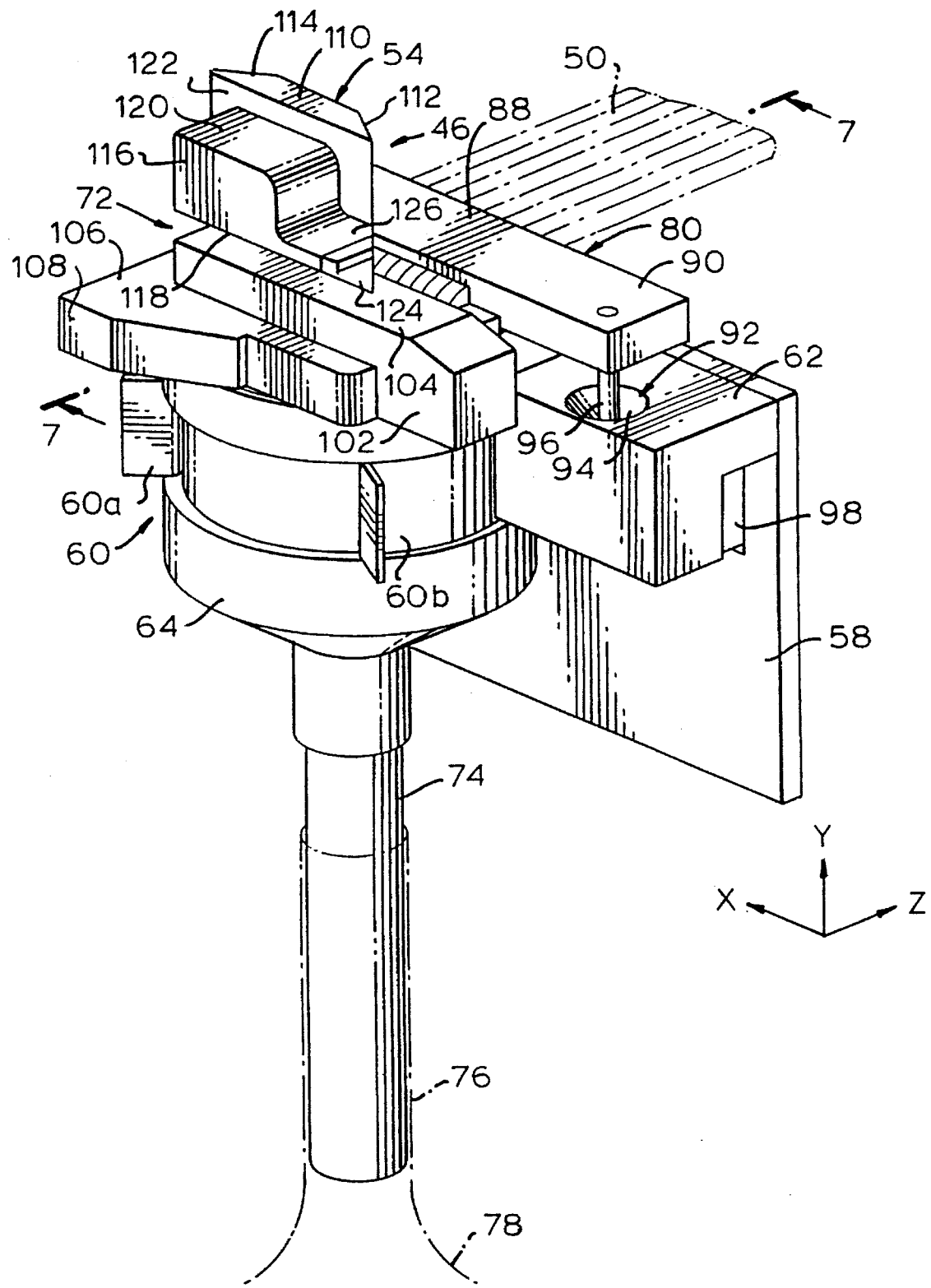
FIG. 2 is a perspective view of part of the apparatus seen in FIG. 1 viewed from the opposite side of the apparatus and seen at an enlarged scale to better depict details of the structure.
Figure 3:
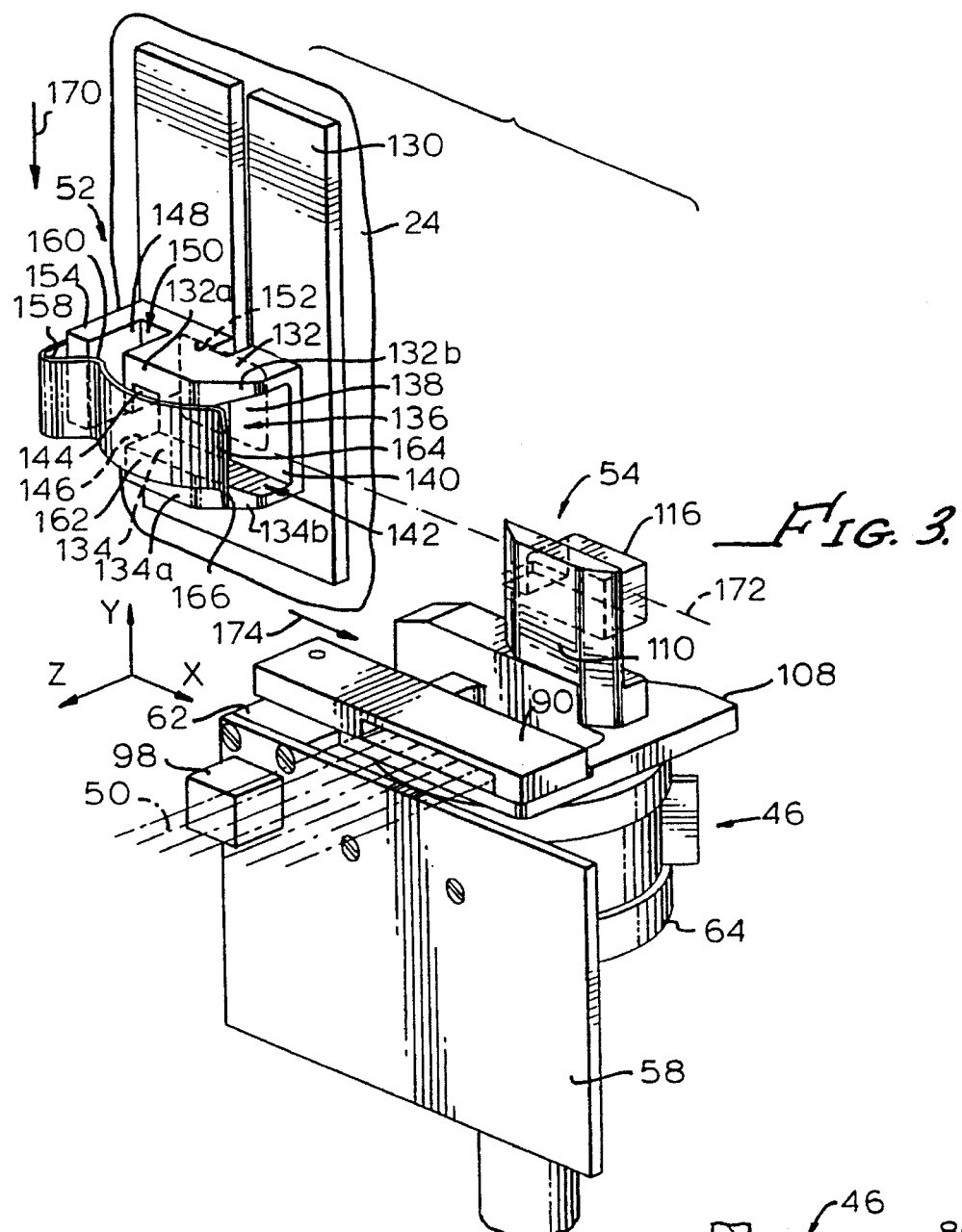
FIG. 3 is a fragmentary perspective view similar to FIG. 1, shown at an enlarged scale, and depicting cooperating parts of the structure in a particular operating relationship preparatory to moving to another operative relationship.
Figure 7:
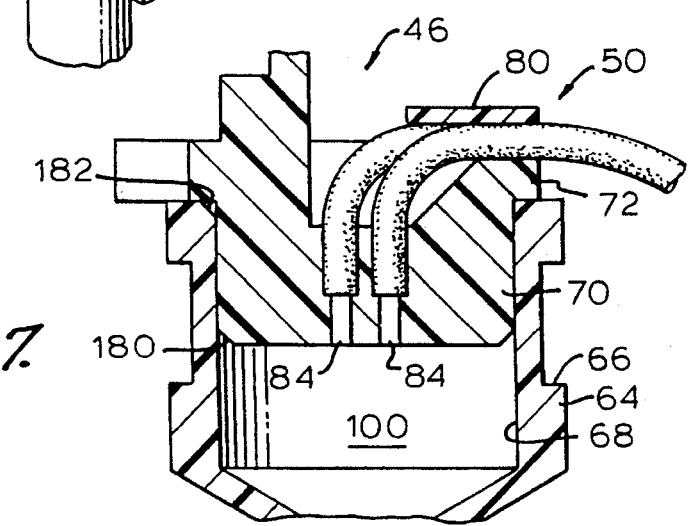
Figure 4:
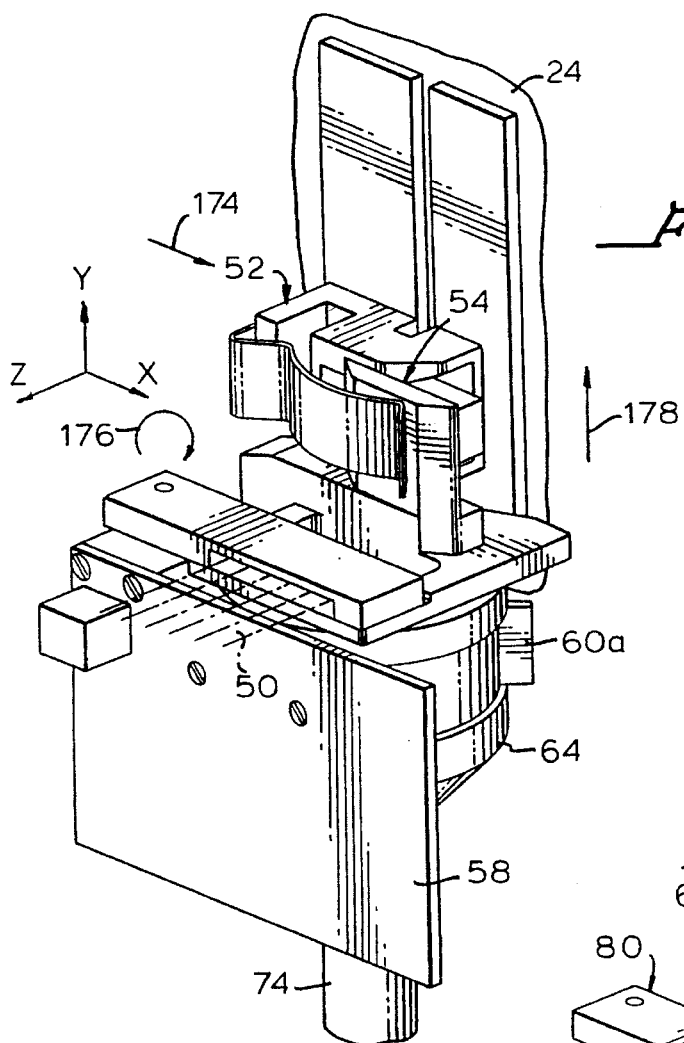
Figure 5:
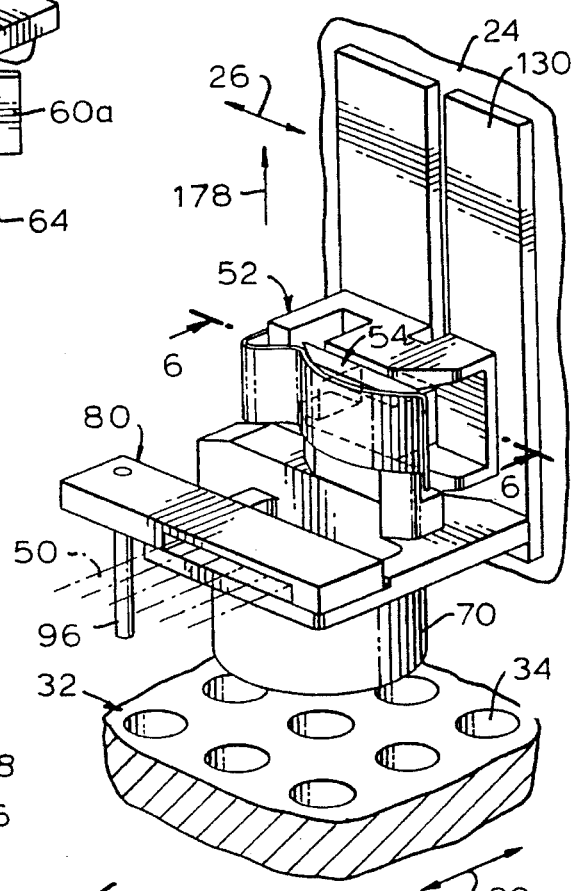
Figure 6:
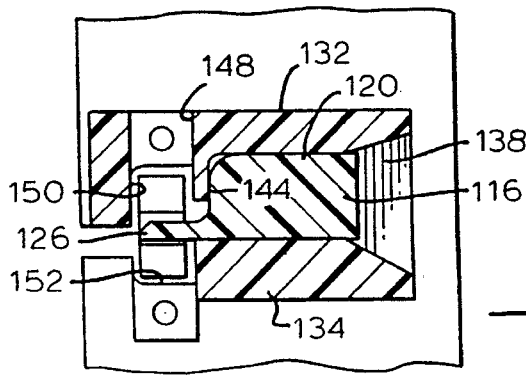

FIG. 4 provides a fragmentary perspective view like FIG. 3, but showing the cooperating parts of the structure in transition from the operative relationship seen in FIG. 3 toward another operative relationship;

FIG. 5 depicts the cooperating parts seen in FIGS. 3 and 4 after they have completed their transition to a docked cooperative relationship and have moved to another operative position;

FIG. 6 provides a fragmentary cross sectional view taken along line 6—6 of FIG. 5; and FIG. 7 provides a fragmentary cross sectional view taken along line 7—7 of FIG. 2.

DETAILED DESCRIPTION OF AN EXEMPLARY PREFERRED EMBODIMENT

Figure 1:
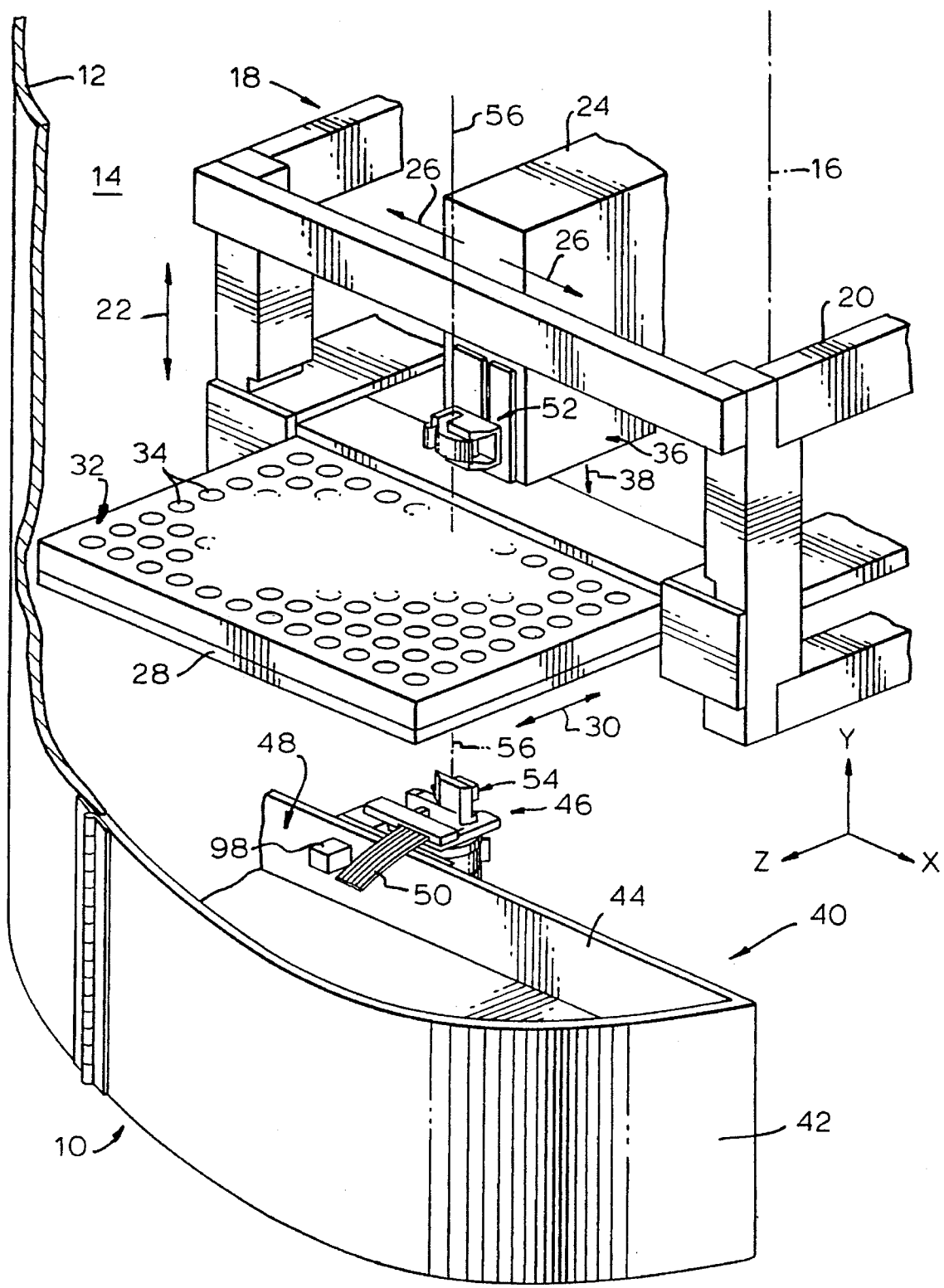

Considering first FIG. 1, an analyzer 10 is fragmentarily depicted. The analyzer 10 includes a circumferentially continuous housing 12, only a fragmentary arcuate outer part of which is depicted in FIG. 1, and which inwardly defines an incubation chamber 14. The incubation chamber 14 is annular, vertically extending, and surrounds a central vertical column (schematically depicted at 16) which extends upwardly in the incubation chamber 14. Carried on the column 16 for vertical movement in the incubation chamber is a carrier member 18. This carrier member 18 is depicted in FIG. 1 at an enlarged scale relative to the size of the housing 12 in order to better illustrate details of the structure of the carrier member. The carrier member 18 includes an open rectangular frame 20, which is vertically movable on the column 16, as is represented by the double-headed arrow 22. The frame 20 slidably carries a shuttle member 24 which is movable from side to side, as is represented by double arrows 26. Also slidably carried by the frame 20 is an extensible shelf member 28, which is movable radially outward and inward of the carrier member 18, as represented by the arrows 30. Upon the shelf, a specimen tray 32 is disposed.

The incubation chamber 14 includes a plurality of such specimen trays, each carried in one of a plurality of respective vertically elongate racks (not shown) on an annular carousel (also not shown) which is rotational about the column 16. Each of the rotational movements of the carousel, the vertical movements of the carrier is on column 16, the lateral movements of the shuttle 26, and the extension and retraction movements of the shelf 28 on the carrier 18, are effected by respective servo motors (not shown), under the control of a controller (also not shown). As a convenience and aid to the reader, a coordinate reference system is noted on FIG. 1, and is referred to hereinafter consistently with respect to this Figure and the other drawing Figures. The carrier member 18 is movable only along a Y axis, while the shuttle member 24 moves only along an X axis, and the shelf 28 extends and retracts only along a Z axis, keeping in mind that the shuttle and shelf members are carried in vertical movement with the carrier 18.

In operation of the analyzer 10 the carousel brings a respective rack of specimen trays in front of the carrier 18, which is elevated to bring the shelf 28 to a level just below the particular specimen tray upon which processing functions are to be performed. The extensible shelf 28 is then extended into the rack under the specimen tray, elevated slightly by vertical movement of the carrier member 18 on column 16 to lift the tray 28 from the rack, and withdrawn into .the frame 20 so that the selected specimen tray 32 is carried along as seen in FIG. 1. As noted above, the specimen tray 32 includes multiple recesses, which are referenced on FIG. 1 with the numeral 34, into which a sample of specimen material may be placed for incubation and analysis. As an example, the specimen tray 32 may include ninety-six recesses 34 arranged in eight rows of twelve recesses each. Of course, other arrangements of the recesses on the tray 32 are possible.

Within the frame 20, the tray 32 is traversed beneath a photometric analyzer (not shown) by movement of the shelf 28 along the Z axis. The photometric analyzer has a sensor head aligning with each column of recesses so that the entire content of the tray 32 can be photometrically analyzed with only traversing of the tray 32 with shelf 28. On the other hand, the shuttle member 24 carriers a fluoroscopic analyzer, generally referenced with the numeral 36. This fluoroscopic analyzer has a single sensing axis, which is referenced with the numeral 38. In order be align the sensing axis 38 with any selected recess 34, the shuttle member 24 is traversed along the X axis across the tray 32, while the tray is traversed with shelf 28 along the Z axis until the selected recess is disposed under the axis 38.

In order to provide for the addition of liquid reagents to the recesses 34, the analyzer 10 includes a fluid dispensing station 40 at a vertical level below the incubation chamber 14. The column 16 extends below the incubation chamber 14 to traverse the fluid dispensing station 40. This fluid dispensing station 40 includes a hinged arcuate wall portion 42 which defines a part of the outer wall of the analyzer 10. Spanning the arcuate wall portion 42 is an interior partition wall part 44 upon which is mounted a fluid dispensing assembly, generally referenced with the numeral 46. This fluid dispensing assembly 46 includes a plural reagent liquid source, which is referenced with the numeral 48, and which can be replenished by outward hinging of the wall part 42. While most of the reagent liquid source 48 is disposed between the walls 42 and 44 so that it is not visible in FIG. 1, this source includes plural flexible reagent liquid supply tubes, the group of which is referenced with the numeral 50, and plural individual reagent liquid sources communicating via the tubes 50 with the dispensing assembly 46. In other words, each tube of this group 50 individually brings a liquid reagent from the source 48 to the dispensing assembly 46.

Viewing now FIGS. 1, 2, and 3 in conjunction, it will be seen that the shuttle member 24 carries a docking fixture 52, and the fluid dispensing assembly 46 includes a docking receptacle 54. While these structures will be described in greater detail below, the reader should note that a vertical line 56 parallel with the Y axis through the docking fixture 52 intersects the docking receptacle 54 when the shuttle member 24 is centered on the carrier 18. Viewing FIG. 2, it is seen that the fluid dispensing assembly 46 includes a base plate portion 58 securing to the Wall 44. Inwardly from this base plate 58 extends both a U-shaped spring steel bracket 60, having a pair of spaced apart legs 60a, and 60b, and a dual-purpose locating lug 62.

In the bracket 58 a funnel member 64 is removably received at an outer circumferential groove 66 thereof. The funnel member 64 defines an upwardly open cylindrical bore 68, best seen in FIG. 7, into which is removably but snugly received a depending cylindrical portion 70 of a fluid dispensing head 72. The funnel member 64 also includes a depending spout portion 74 over which is received a neck portion 76 of a depending catch bag 78 (only a part of which is visible in FIG. 2). The catch bag 78 is supported on an inwardly extending shelf portion (not shown) of the fluid dispensing station 40.

The fluid dispensing head 72 includes the depending portion 70 as well as the docking receptacle 54, and a laterally extending dual-function retention and locating bar portion 80 (seen in FIG. 2). Depending portion 70 is circular in plan view. Viewing FIG. 7, it is seen that the depending portion 70 of the fluid dispensing head 72 defines plural stepped through bores 82. Into these bores 82, respective ends of the tubes 50 are received. A lower smaller diameter portion 84 of the bores 82 opens on a lower face 86 of the cylindrical portion 70. These smaller diameter bore portions 84 define the individual nozzles through which respective liquid reagents will be dispensed to the recesses 34 of the sample tray 32. The retention and locating bar 80 includes a retention portion 88 which overlies and retains the reagent tubes 50. As is seen in FIG. 2, this bar member 80 also includes an extension portion 90 which extends to and over the locating lug 62. This locating lug 62 defines an upwardly opening bore 92 which at its upper extent includes a funnel shaped portion 94. From the extension portion 90 of the bar 80 a locating pin 96 depends into the bore 92. Because the depending portion 70 of the fluid dispensing head 72 and the bore 68 of funnel member 64 are both round in plan view, the locating pin 96 in bore 92 alone establishes a rotational orientation for the dispensing head 72 on the fluid dispensing assembly 46. The locating lug 64 also includes an optical sensor 98 which provides a signal indicative of the presence of the locating pin 96 in the bore 92. Hence, the presence of the dispensing head 72 on the funnel 64 is communicated to a controller (not shown) for the analyzer 10.

Depending portion 70 of dispensing head 72 is snugly but removably received in the cylindrical bore portion 68 of the funnel member 64. Consequently, the nozzles 84 open into a chamber 100. This chamber 100 communicates with the interior of the reagent catch bag 78 via the spout 74 and the snugly fitting bag neck 76. Thus, reagents received into the bag 78 and communicating their volatile constituents to the chamber 100 provides an environment within this chamber which discourages evaporation of reagents from the dispensing head 72. Additionally, the snug fit of the depending portion 70 in the bore 68 tends to isolate the chamber 100 from the environment outside this chamber while the dispensing head is resting on the funnel member 64 to further reduce the evaporation of reagents from the dispensing head 72 and tubes 50 leading thereto.

Viewing FIGS. 1, 2, and 3, in conjunction, and with particular attention now to FIG. 2, it is seen that the docking receptacle 54 includes an elongate laterally extending lug portion 102 defining an upper laterally extending guide surface 104. From the lug portion 102, an inwardly extending boss 106 extends to define an inwardly disposed abutment surface 108. Above the lug portion 102 a wall portion 110 extends upwardly to define both first 112 and a second 114 vertically extending chamfer surfaces. Inwardly from the wall portion 110 extends a laterally extending support lug portion 116 having a lower laterally and inwardly extending support and guide surface 118 and an upper laterally extending guide surface 120 which is above and parallel with the surface 104. The support and guide surface 118 confronts the surface 104. Respectively above and below the surfaces 120 and 118, and perpendicular thereto, the wall portion 110 defines respective spaced apart laterally extending abutment surfaces 122 and 324. Also, the support lug 116 defines a laterally extending tongue portion 126 extending from the remainder of this lug along the support wall portion 110.

Turning to FIG. 3, the docking fixture 52 is seen to include a mounting plate 130 which secures to the shuttle member 24. On the mounting plate, a pair of vertically spaced apart and laterally extending support wall portions 132 and 134 extend outwardly. Each support wall portion 132 and 134 defines a respective outwardly disposed and laterally extending abutment surface 132a, and 134a, respectively. These abutment surfaces 132a and 134a each include respective entrance chamfer sections 132b and 134b. The support wall portions at one end (closest to the viewer of FIG. 3) are chamfered and define between them a laterally extending support lug cavity 136. A rear wall 138 of the support lug cavity is also chamfered at 140 so that the entrance 142 to the support lug cavity 136 is funnel-shaped.

An end wall 144 of the support lug cavity depends from the upper support wall portion 132 toward but short of the lower of the support wall portions 134 to define a laterally open notch 146. A vertically extending notch 148 intersects with and communicates with the notch 146. Communicating with the vertical notch 148 is an outwardly extending passage 150 (best seen in FIG. 6) communicating also with a window 152 opening through the mounting plate 130. As is seen in FIG. 7, an optical sensor 154 is mounted to the mounting plate 130 and extends into the window 152 in order to sense the presence of the support lug 116 in the support lug cavity 136, when these two features are fully engaged as is indicated by the projection of tongue 126 through notch 144, as will be further explained.

An outwardly extending mounting wall portion 156 extends from the mounting plate 130 to carry a formed spring steel spring member 158. This spring member 158 includes a recurve section 160 adjacent to its attachment to the mounting wall portion 156, a first cusp 162 leading to an arcuate portion 164 extending laterally across and outwardly of the support lug cavity 136 to a second cusp 166, and an outwardly turned entrance guide section 168.

FIG. 3 also illustrates the movement of docking fixture 52 first vertically downward (along the Y axis) with the carrier member 18 (as is indicated by arrow 170) to a level such that the support lug cavity 136 is in alignment along a laterally extending line 172, which parallels the X axis, with the support lug cavity 136. In order to make this downward movement of the carrier member 18 possible in preparation to engagement of the docking fixture 52 with docking receptacle 54, the shuttle member 24 is offset to the one side of its centered position, as is seen in FIG. 3, so that the open entrance 142 of the cavity 136 is disposed toward the docking receptacle 54. Subsequently, the shuttle member 24 is moved laterally along the X axis (as indicated by arrow 174) to engage the wall portion 110 at its first chamfer 112 between the entrance guide section 168 of the spring member 158 and the entrance chamfers 132b and 134b of the abutment surfaces 132a and 132b. Also, the support lug 116 enters the support lug cavity 136, as is seen viewing FIG. 4. As FIG. 4 depicts, the movement of the docking fixture 52 along the X axis into engagement with the docking receptacle 54, as is represented by the arrow 174 results in a clockwise torque indicated with arrow 176. However, the dispensing head 72 is prevented from rotating in the funnel 64 by the engagement of pin 96 in bore 92 of location lug 62, recalling the description of FIG. 2.

The movement of shuttle member 24 along the X axis to effect engagement of the docking fixture 52 with the docking receptacle 54 is continued until the support lug 116 is fully received into the support lug cavity 136, viewing FIG. 7 once again. As will be further explained, this condition of full engagement of the docking fixture 52 with the docking-receptacle 54 fixes the positional relationship of the dispensing head 72 with respect to the shuttle 24 in each of the X-Y-Z directions, as well as in the rotational planes which are defined cooperatively by these coordinate axes. FIG. 4 also shows that once complete engagement of the dispensing head 72 on the shuttle 24 is achieved, the carrier 18 is moved vertically upward along the Y axis in a third movement represented by arrow 178. This vertically upward movement lifts the dispense head 72 at its cylindrical portion 70 out of the bore 68 of the funnel member 64. Also, the pin 96 is withdrawn from the bore 92 of locating lug 62 so that the sensor 98 indicates that the dispensing head is absent from its position on the funnel 64.

As FIG. 5 depicts, the vertically upward movement (arrow 178) of the dispensing head 72 with carrier 18 is only of such an extent as to allow the shelf 28 and sample tray 32 to be extended under the lower portion 70 of the dispense head 72. Arrows 26 and 30 are repeated on FIG. 5 in order to represent how the shelf 28 is extended or retracted and shuttle 24 is moved laterally side to side to bring a selected one of the fluid dispensing nozzles 84 into vertical congruence with a selected recess 34 of the tray 32. When this alignment is achieved, reagent liquid from the source 48 is dispensed via the tubes 50 and dispense head 72 into the selected receptacles of the tray 32. The flexibility of the tubes 50 allows for the limited vertical movement of the dispense head 72 above the funnel 64, and the lateral movement of this head with the shuttle member 24 as is necessary to bring the selected nozzles 84 into alignment with the selected recesses 34 of the tray 32.

When dispensing of reagents from the source 48 into recesses 34 of the selected tray 32 is completed, the shuttle member 24 is centered on carrier 18 to align the dispense head 72 above funnel member 64. Subsequently, the three axial movements which were require a to achieve docking and deployment of the dispense head are repeated in the reverse order in order to store and undock from the dispense head. In other words, the three axial movements which were required to dock with and deploy the dispense head 72 were: first, a vertical movement of the carrier to a level where the shuttle member 24 is in alignment with and along side of the dispense head; second, a lateral movement of the shuttle member 24 to engage the docking fixture 52 with the docking receptacle 54; and third, a vertically upward movement of the carrier member 18 to withdraw the dispense head 72 from the funnel member 64.

These three movements are repeated in reverse order to store the dispense head 72 on the funnel member 64. As the dispense head 72 vertically approaches the funnel member 64, a lower chamfer 180 on the dispense head 72 in conjunction with an entrance chamfer 182 on the funnel bore 68 (best seen viewing FIG. 7) cooperatively eases the return of the dispense head into the funnel member. Similarly, the funnel shaped portion 94 of the bore 92 in locating lug 62 eases the return of the pin 96 into this bore.

However, it should be emphasized that the precision with which the dispensing head 72 is located on the shuttle member 24 greatly assists this return into the funnel member 64, as well as the certainty of alignment of the dispensing nozzles with a selected recess of the tray 32 during reagent dispensing. Viewing FIGS. 2, 3, 5, and 6 in conjunction, it is seen that the docked dispensing head 72 on the docking fixture 52 has the abutment surface 108 (FIG. 2) engaged with the mounting plate 130 (FIG. 3). Also, the laterally extending horizontal surfaces 104, 118, and 120 (FIG. 2) are engaged with or confronted for engagement with the surfaces of the walls 132 and 134 (FIG. 3). Still additionally, the cusps 162 and 164 of the spring member 158 engage the respective chamfer surfaces 112 and 114 of the support wall 110 (FIGS. 2 and 3) to also urge the abutment surfaces 122 and 124 (FIG. 2) into engagement with the end abutment surfaces 132a and 134a on the docking fixture (FIG. 3).

The identified surfaces of engagement and confrontation between the docking fixture 52 and the docking receptacle 54 are collectively spaced from one another both laterally and vertically as well as horizontally. In net effect, the plurality of engaging and confronting surfaces defined between the docking fixture and receptacle provides for supporting the weight of the dispense head as well as applying vertical force thereto in both directions as necessary to disengage and reengage this head from the funnel member 64. Further, the relative positional relationship of the head and docking fixture is set by the cooperation of the spring cusps with the support wall chamfers and the abutment surfaces of the wall portion 110 with the support walls 132, 134.

The only degree of freedom which the support head has relative to the docking fixture is in the direction of lateral movement which disengages the support lug 116 from the support cavity 136. This movement of the dispensing head is possible in opposition to the spring member 158 only with the exertion of a certain force thereon. This force level could not be exerted by the flexible tubes 50 because they are relatively flexible and are never extended beyond their length by the traversing movements of the shuttle member 24. Only the firm support and location provided to the dispense head 172 by its location at its lower portion 70 in the bore 68 of funnel member 64 can provide the necessary restraint on the dispense head so that this head can be removed from the docking fixture by lateral movement of the shuttle 24. The result is a very high certainty of positional location for the dispense head 72. This head is either on the funnel member 64, as verified by the signal from the sensor 98, or on the shuttle member 24, as verified by the signal from sensor 154.

The present invention provides a fluid dispensing apparatus and method in which greater certainty of placement of the fluid dispensing head in both its storage location and in its fluid dispensing location is provided. The fluid dispensing head in its storage location cooperates with the funnel member to define an environmentally isolated chamber which reduces the evaporation of volatile constituents from the reagent liquids, as well as decreasing exposure of the remainder of the analyzer to the potentially corrosive effects of the reagents. Additionally, the funnel member 64 may be removed easily from the U-shaped bracket 60 to allow cleaning of this funnel member and disposal of the reagent which is received into the catch bag 78.

While the present invention has been depicted, described, and is defined by reference to a particularly preferred embodiment of the invention, such reference does not imply a limitation on the invention, and no such limitation is to be inferred. The invention is capable of considerable modification, alteration, and equivalents in form and function, as will occur to those ordinarily skilled in the pertinent arts. The depicted and described preferred embodiment of the invention is exemplary only, and is not exhaustive of the scope of the invention. Consequently, the invention is intended to be limited only by the spirit and scope of the appended claims, giving full cognizance to equivalents in all respects.

I claim:

1. In a chemical analyser having a vertically and horizontally movable carrier member and a fluid dispensing head with plural fluid dispensing nozzles which is removably received into a storage location therefor, a method of precisely and reliably attaching said fluid dispensing head supportingly and removably with said carrier member while said fluid dispensing head is in said storage location preparatory to vertical movement of said fluid dispensing head from said storage location with said carrier member and the dispensing from said fluid dispensing nozzles of said fluid dispensing head of fluid to preselected receptacles therefor; said method including the sequential steps of:

a) providing said carrier member and said fluid dispensing head with cooperating means for selectively supportingly securing said fluid dispensing head to said carrier member in response to a movement of said carrier member consisting essentially of a horizontal movement thereof while horizontally aligned with said fluid dispensing head;

b) configuring said cooperating means such that each of said carrier member and said fluid dispensing head respectively define one of a docking fixture and a docking receptacle which are inter-engageable with one another in response to relative movement along a horizontal axis;

c) forming said docking fixture to include a cavity which extends parallel with said horizontal axis, and forming said docking receptacle to include a support lug extending parallel with said horizontal axis and which is supportingly receivable into said cavity;

d) moving said carrier member downwardly along a vertical axis to a position of alignment with said fluid dispensing head along said horizontal axis;

e) moving said carrier member horizontally to engage said carrier member with said fluid dispensing head while the latter is held in said storage location; and f) moving said carrier member upwardly along said vertical axis to withdraw said fluid dispensing head from said storage location.

2. The method of claim 1 further including the steps of providing a yieldable resilient member carried by one of said cooperating means and removably cooperatively retaining said cooperating means interengaged with one another, wherein said yieldable resilient member includes a pair of horizontally spaced apart cusps, and the other of said cooperating means includes a support member having a pair of horizontally spaced apart chamfers each of which is engaged by a respective one of said cusps to relatively position and removably retain said cooperating means while the latter are supporting said fluid dispensing head from said carrier member.

3. The method of claim 1 further including the steps of configuring said storage location and fluid dispensing head to allow relative withdrawal motion therebetween only along said first axis.

4. The method of claim 1 further including the steps of configuring said storage location and said fluid dispensing head to cooperatively define a substantially closed chamber, and communicating a fluid dispensing nozzle of said head with said chamber.

* * * * *